(12) United States Patent
Willemin (10) Patent No.: US 7,372,252 B2
(45) Date of Patent: May 13, 2008

(54) AUTOMATED PLATFORM FOR ELECTRONIC APPARATUS ENVIRONMENTAL TESTING & METHOD OF USE

(75) Inventor: Daniel Ray Willemin, Austin, TX (US)

(73) Assignee: Professional Testing (EMI), Inc., Round Rock, TX (US)

( * ) Notice: Subject to any disclaimer, the term of this patent is extended or adjusted under 35 U.S.C. 154(b) by 126 days.

(21) Appl. No.: 11/301,417

(22) Filed: Dec. 13, 2005

(65) Prior Publication Data
US 2007/0132474 A1    Jun. 14, 2007

Related U.S. Application Data

(60) Provisional application No. 60/708,566, filed on Aug. 16, 2005.

(51) Int. Cl.
*G01R 31/00* (2006.01)

(52) U.S. Cl. .................................................. 324/158.1

(58) Field of Classification Search ........ 324/760–765, 324/158.1
See application file for complete search history.

(56) References Cited

U.S. PATENT DOCUMENTS

| | | | | |
|---|---|---|---|---|
| 3,709,026 A | * | 1/1973 | Rhodes et al. | 73/12.11 |
| 4,572,283 A | * | 2/1986 | Vanderschaaf | 165/61 |
| 4,782,291 A | * | 11/1988 | Blandin | 324/158.1 |
| 5,093,984 A | * | 3/1992 | Lape | 29/741 |
| 5,638,003 A | * | 6/1997 | Hall | 324/514 |
| 6,373,270 B1 | * | 4/2002 | Cochran et al. | 324/760 |
| 7,038,441 B2 | * | 5/2006 | Stoll et al. | 324/158.1 |

* cited by examiner

*Primary Examiner*—Vinh P. Nguyen
(74) *Attorney, Agent, or Firm*—Hulsey IP Intellectual Property Lawyers, P.C.

(57) ABSTRACT

An automated platform for electronic apparatus environmental testing and the methods of its operation holds and positions electronic devices during environmental testing. The automated platform may be a multi-legged table and includes a surface for providing vertical support. A plurality of bracket mechanisms, each hold in position an electronic device. A bracket positioning mechanism associates with the plurality of bracket mechanisms for controllably positioning the bracket mechanisms. Control circuitry associated with the bracket turntable controls the positioning of the bracket mechanisms. At least one brush mechanism may be positioned in association with the bracket mechanisms for brushing said bracket mechanisms and an electronic device held in position by said bracket mechanism.

20 Claims, 11 Drawing Sheets

AUTOMATED PLATFORM FOR ELECTRONIC APPARATUS ENVIRONMENTAL TESTING & METHOD OF USE

CROSS REFERENCE TO RELATED APPLICATIONS

This application claims the benefit of priority to U.S. Provisional Patent Application No. 60/708,566 entitled "DUST SYSTEM," by Dave Rahe, et al. filed on Aug. 16, 2005, and is incorporated herein by reference in its entirety for all purposes.

FIELD

The disclosed subject matter relates to electronic systems and methods of their testing. More particularly, this disclosure relates to a novel and improved automated platform for electronic apparatus environmental and other testing scenarios and methods of using such a platform.

DESCRIPTION OF THE RELATED ART

Many different contaminants and reliability degradation factors may be encountered in the atmosphere to which electronic systems are exposed. Some of the more common contaminants include moisture, sand, dust, and corrosive airborne chemicals. Each of these potentially degrading atmospheric conditions must be recognized and adequately addressed in the electronic systems design. However, in order to effectively design to these considerations, there is the need to understand their effects on the electronic systems.

For example, sand and dust degrade equipment primarily by abrasion leading to increased wear, friction causing both heat and increased wear, and the clogging of filters, small apertures, and delicate equipment. Equipment with moving parts, such as ventilation fans and the like, requires particular care when designing for sand and dust protection. Sand and dust will abrade optical surfaces, either by impact when being carried by air, or by physical abrasion when the surfaces are improperly wiped during cleaning. Dust accumulations have an affinity for moisture and when combined with moisture may lead to corrosion, electrical shorts, or the growth of fungus.

Dust may be composed of any fine, dry particulate material including metals, combustion products, solid chemical contaminants, and so on. Some forms of dust may provide direct corrosion or fungicidal effects on equipment, since dust may be alkaline, acidic, or microbiological. Dust may also include numerous fibers and fiber particles. As dust accumulates, these fibers may associate with one another and further clog or impede air flow in electronic systems.

Most electronic systems require air circulation for cooling, so removing dust is not a simple matter. The question with such ventilated electronic systems is not whether to allow dust to enter, but rather how much or what size dust can be tolerated. The problem becomes one of filtering the air to remove dust particles larger than a specific nominal size. The nature of filters is such that for a given working filter area, as the ability of the filter to stop smaller and smaller dust particles increases, the flow of air or other fluid through the filter decreases. Therefore, the filter surface area either must be increased, the flow of fluid through the filter decreased, or the allowable parted size increased. That is, invariably there must be a compromise.

A particularly challenging situation may arise when dust fibers deposit within surfaces designed for heat dissipation within such electronic systems. An example of such heat dissipation surface is the heat dissipation device used in many laptop computers, wherein a thermally conductive metal provides a heat sink from the electronic circuitry to the local air within the laptop chassis. In the event that fibrous dust particles coagulate across and prevent air ventilation through such heat sink devices, excessive circuit temperatures may occur rapidly. These rapid and, oftentimes prolonged excessive temperatures may cause unnecessary power consumption, circuit damage, operating performance degradation, and other undesirable results.

Internal dust will also adversely affect open mechanical devices, causing wear and deterioration. Electrostatic room air filters are available which will remove even micron sized dust and smoke particles. Valuable in normal environments, this type filter should seriously be considered in dusty or smoky industrial locations. Accordingly, having a clear understanding of the engineering requirements for such devices is important, and obtaining such information oftentimes requires specific testing environments capable of rapidly replicating actual use environments.

That is, one of the particular challenges in testing for the effects of environmental contaminants on electronic systems relates to time required to sense and experience the contaminants' adverse effects. For example, with dust many months may be needed to create an overheating situation, because dust fibers will accumulate over heat dissipation surfaces only slowly. However, when they do, the effects of such accumulation can be devastating. With new laptop computer and desktop computer designs evolving rapidly, there may not be the ability to develop a complete understanding of the ill effects of such contaminants in the design process. A need exists, therefore, for a way to determine more rapidly the effects of dust and other particulates in the operation of such electronic systems.

Another feature of such environments is the need to provide reliable and uniform test results. It has been shown that certain difficulties exist in environmental chambers designed to be deliver airborne particulate to electronic devices. An optimal environmental chamber for particulate would have the ability to hold and test a variable number of electronic devices. For example, for some testing a single electronic device, e.g., a laptop, may be sufficient to gather the desired testing data. However, other tests may require the testing of four or more such electronic devices simultaneously.

Because of the size and density of such particulate, providing a uniformly distributed amount of the particulate to each electronic device that may be within the environment chamber may be a difficult undertaking. Moreover, because of testing considerations and human factors, stopping a test to reposition electronic devices or otherwise entering the test environment for other changes is not desirable. Breaking the test environment may cause unreliable test results. At the same time, exposure to airborne particulate can be dangerous to test personnel.

Still another consideration is the need to perform within the same environmental test chamber both active and passive testing support. For example, during active testing, there is the need to assure that ventilation passages and associated filters remain clear of dust or particulate. This assures that a maximum amount of particulate actually reaches the innermost parts of the electronic device, thereby assuring a thorough testing regimen. Components for holding the electronic devices need to accommodate both active and passive testing regimens, where active tests involve the active deposition of particulate matter proximate to electronic devices and passive testing involves placing an electronic device proximate to a previously dusted surface.

A need exists, therefore, for system and process that allows for location to location consistency of multiple electronic devices within an environmental particulate or contaminate chamber.

Furthermore, a need exists for a method and system for automated means supporting active testing of electronic devices, while also providing for the efficient control and monitoring of passive testing.

Still further, such a system must be economical to manufacture and easy to control automatically and from a controller outside the testing environment.

SUMMARY

The automated platform for electronic apparatus environmental testing and the methods of its operation here disclosed apply to the environmental testing of a wide variety of electronic systems. Although the disclosed embodiments may relate to a platform useful for the testing of particulate contaminants and, even more particularly, to fibrous dust particles, the automated platform may be adapted in other embodiments for use in testing the effects of a variety of contaminants and environmental conditions, including moisture, airborne chemicals, sand, and even excessive temperatures and temperature transients.

According to one aspect of the disclosed subject matter, therefore, an automated platform for electronic apparatus environmental testing and the methods of its operation holds and positions electronic devices during environmental testing. The automated platform may be a multi-legged table and includes a surface for providing vertical support. A plurality of bracket mechanisms, each hold in position an electronic device. A bracket positioning mechanism associates with the plurality of bracket mechanisms for controllably positioning the bracket mechanisms. Control circuitry associated with the bracket turntable controls the positioning of the bracket mechanisms. At least one brush mechanism may be positioned in association with the bracket mechanisms for brushing said bracket mechanisms and an electronic device held in position by said bracket mechanism. In one embodiment, the brush mechanism may be a rotating brush mechanism positioned for rotating and brushing the bracket mechanism and an associated electronic device. In operation, the rotating brush mechanism removes particulate contamination from said bracket mechanism and said electronic device. In another embodiment, the bracket positioning mechanism may be a bracket turntable for rotating the plurality of bracket mechanisms about a platform axis.

These and other aspects of the disclosed subject matter, as well as additional novel features, will be apparent from the description provided herein. The intent of this summary is not to be a comprehensive description of the claimed subject matter, but rather to provide a short overview of some of the subject matter's functionality. Other systems, methods, features and advantages here provided will become apparent to one with skill in the art upon examination of the following FIGURES and detailed description. It is intended that all such additional systems, methods, features and advantages that are included within this description, be within the scope of the accompanying claims.

BRIEF DESCRIPTIONS OF THE DRAWINGS

The features, nature, and advantages of the disclosed subject matter will become more apparent from the detailed description set forth below when taken in conjunction with the drawings in which like reference characters identify correspondingly throughout and wherein.

DETAILED DESCRIPTION OF THE SPECIFIC EMBODIMENTS

The disclosed subject matter addresses the many aspects of testing ventilated electronic systems. In particular, the present disclosure has application for active testing of the effects of active dust and other airborne contaminants on ventilated electronic systems. In a controlled environment established by the environmental chamber system, "settling dust" is produced that permits the simulation of months and years worth of normal operational environments into which electronic systems may be used. Moreover, the disclosure provides a method and system allow for the introduction of suspended dust into the electronic equipment, while cleaning vents at regular cycles and permitting the continual addition of dust into the environmental chamber. The result is a much shorter time to electronic systems failure, which provides valuable information relating to the equipment's design performance. In addition, the environmental testing assembly provides the ability to measure and monitor the response of the electronic systems in the failure modes of operation, and, therefore, understand of the most susceptible portions of the tested electronic systems.

Figure 1:
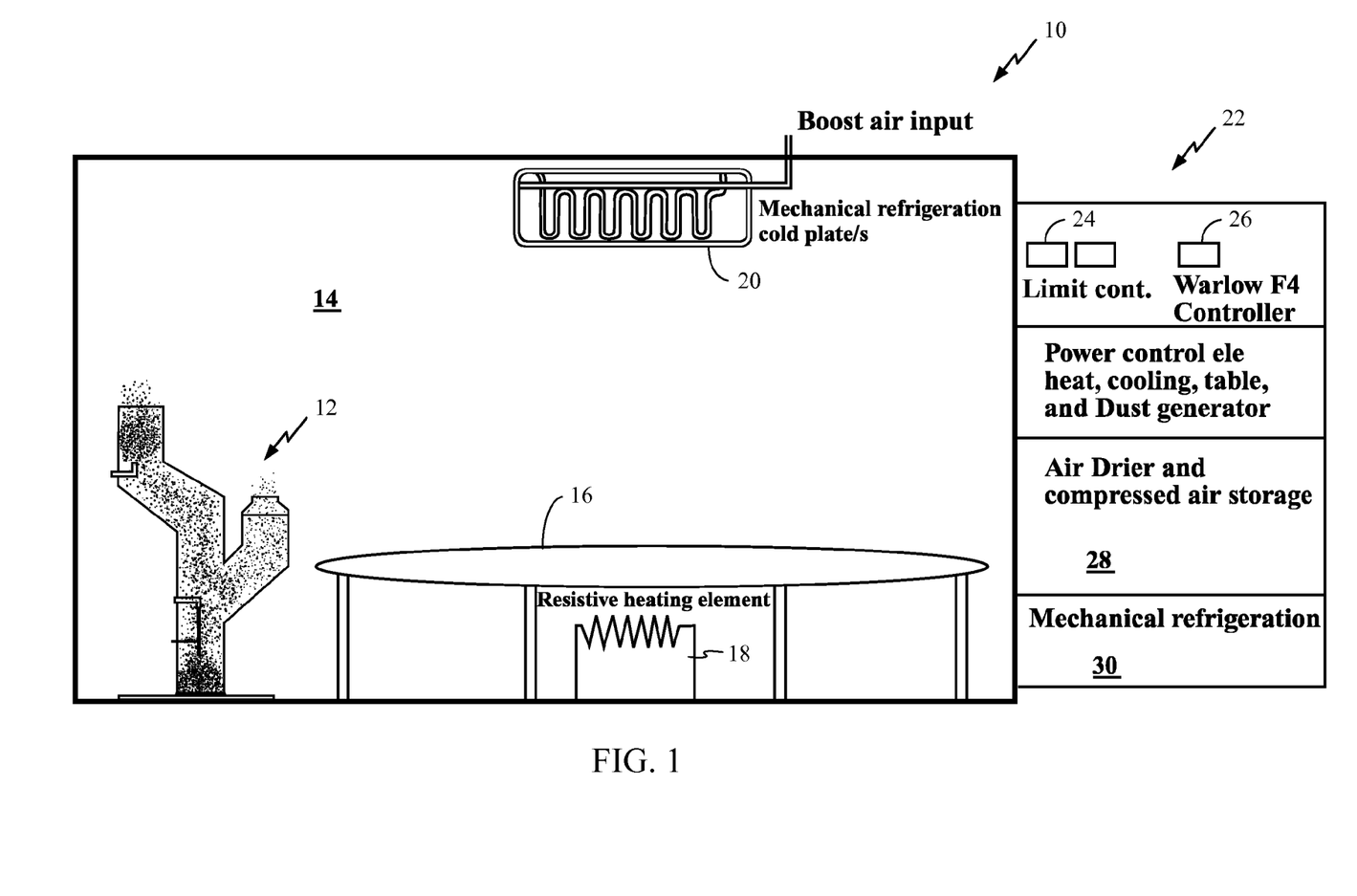
FIG. 1 shows a testing system for electronic devices according to the disclosed subject matter.

FIG. 1 shows one embodiment of the disclosed subject matter as environmental contaminant testing system 10 for testing the operation of electronic systems in harsh environments. Environment contaminant testing system 10 includes a contaminant delivery system 12, which may deliver airborne contaminants within environmental chamber 14 in the direction of a platform 16. In order to maintain a controlled temperature, environmental chamber 14 includes heating element 18 and cooling element 20. Heating element 18 may function as a resistive heating unit. Cooling element 20 may be a cooling system operating with a combination of air cooling and refrigerant cooling features.

Environmental chamber 14 may contain numerous electronic systems for testing, each of which may include an air intake mechanism that may be susceptible to receiving particulate or airborne contamination and, as a result, excessively heat. Platform 16 can support numerous electronic systems and receive settled amounts of the particulate contamination. Contaminant delivery system 12 delivers the particulate contamination within environmental chamber 14 in the direction of platform 16 and the electronic systems. Contaminant delivery system 12 also includes a mechanism to for controlling the uniformity of the particulate contamination delivered to the electronic systems.

Chamber control cabinet 22 provides compressed air to contaminant delivery system 12 and controls numerous aspects of the supplied air. For instance, chamber control cabinet 22 may include an air contamination control unit 24 and flow regulator 26 for controlling flow to contaminant delivery system 12 and the assuring the highest quality air arrives within environmental chamber 14. In addition, control system 22 includes air dryer unit 28 and various mechanical refrigeration units, all for controlling the quality, quantity, and flow rate of air within environmental chamber 14 that contaminant delivery system 12 provides in the flow of airborne contaminants contamination.

Figure 2:
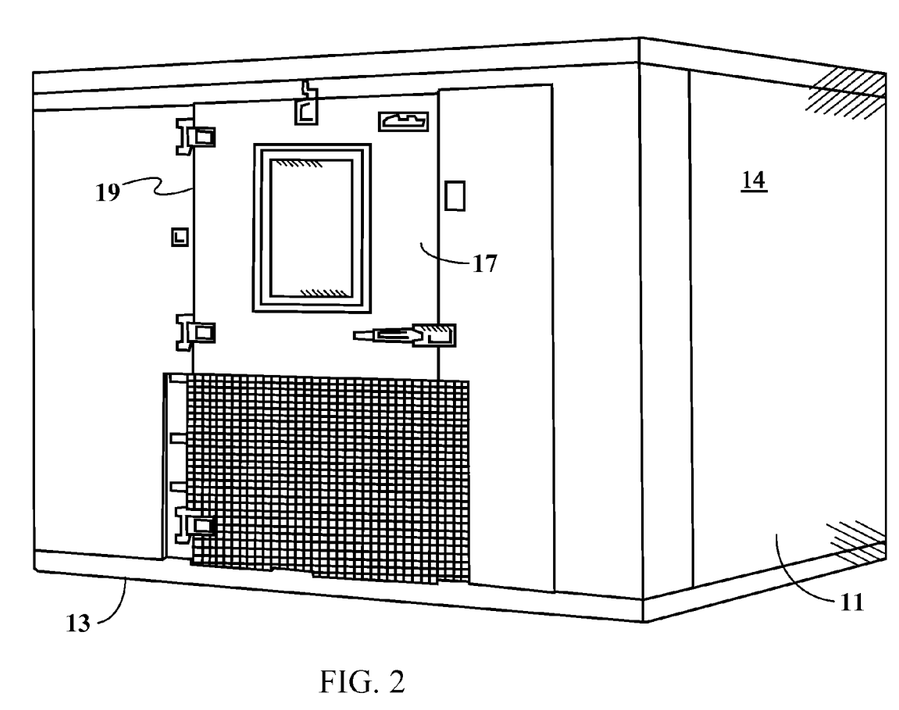
FIG. 2 illustrates one potential embodiment of an environmental chamber for use in the disclosed subject matter.

FIG. 2 illustrates one potential embodiment of environmental chamber 14, which may be a walk-in chamber, such as the Bally 9502136 AC, having, for example, the dimensions of 9'8"×9'8" square lateral dimensions, and a 7'6" height and a 48" door w/window. Such a chamber may include 4" walls 11 and a floor 13 to establish a self-contained environmental chamber. One suitable environment chamber 14 is manufactured by Bally Refrigerated Boxes, Inc. and includes foam core walls which are foamed using HCFC expanding agents and shall meet all current international standards. The walls 11 consist of interior and exterior metals skins precisely foamed with steel and dies and roll-form equipment and are placed into heated molds and liquid urethane injected between them. For extra rigidity, the exteriors of all vertical walls 11 have vertical grooves spaced on centers. Urethane structures are foamed in place and, when completely heat-cured, bind tenaciously to the metal skins to form an insulated wall 11. Walls 11 may contain 100 percent urethane insulation with no internal wood or structural members between the skins. For tight joints, wall edges are preferably foamed-in-place tongues and grooves with a flexible vinyl gasket on the interior and exterior of all tongue edges. Gaskets are resistant to damage from oil.

Walls are equipped with diaphragmatic joining devices. The distance between locks are preferably does not exceed 46" in the disclosed embodiment, and includes a cam action, hooked locking arm placed in one wall, and a steel rod positioned in the adjoining wall, so that when the arm is rotated, the hook engages the rod and draws the walls tightly together with cam action. Arms and rods are housed in individual steel pockets. Pockets on one side of the wall are connected to pockets on the other side in width wide metal straps set into and completely surrounded by the insulation. When walls are joined together, these straps form lock-to-lock connections for extra strength. Floor wall construction is similar to that described, but with a heavier-gauge interior skin; thickness of floor may be different than that of vertical walls.

Environmental chamber 14 may also include a hinged entrance door 17 using magnetic core, thermoplastic gaskets that are installed on the top edge and both sides of the door for keeping the door in a closed position, forming a tight seal. A flexible, dual-blade wiper gasket may be installed at the bottom of door 17. A heavy U-channel structural steel frame 19 may be placed around the perimeter of the door opening for preventing racking or twisting, with the steel frame reinforced for hardware attachment.

Preferably an anti-condensate heater wire may be concealed behind the metal edge of the doorjambs. The door shall also include a vapor-proof interior lamp, junction box for 120 v. 60-cycle, 1-phase, A.C. electricity, a thermometer and weather hoods for outdoor installations.

Chamber control cabinet 22 may be a controller such as provided in the Watlow F-4 controller, including a resistive heat, RH sensor, to provide the needed control of environmental chamber 14. The air, electrical, HVAC control cabinet uses an equipment rack assembly, e.g., such as provided the Technisoft corporation for the cabinet with racks provided by Kendall Howard corporation. Chamber control cabinet 22 may further include a regenerative air drier, as provided by Puregas, Inc., which includes input and output air filters, regulators for air control and purity as a part of air contamination control unit 24. A dry air storage tank (e.g., such as provided by Sears, Roebuck & Company) associates with a cool boost, a pump, and stir regulators to provide controlled air for mixture with particulates herein described. In association with such controls and air conditioning components, necessary gages and sensors will be included.

Heating element 20 may be similar to the Grainger Corporation, 3HMO03 unit, which includes a 1 Kw Bar element. The cooling panel may be a King refrigeration P107C unit connected with a Johnson controls switch and other associated refrigeration and control components, also part of refrigeration unit 30.

Figure 3:
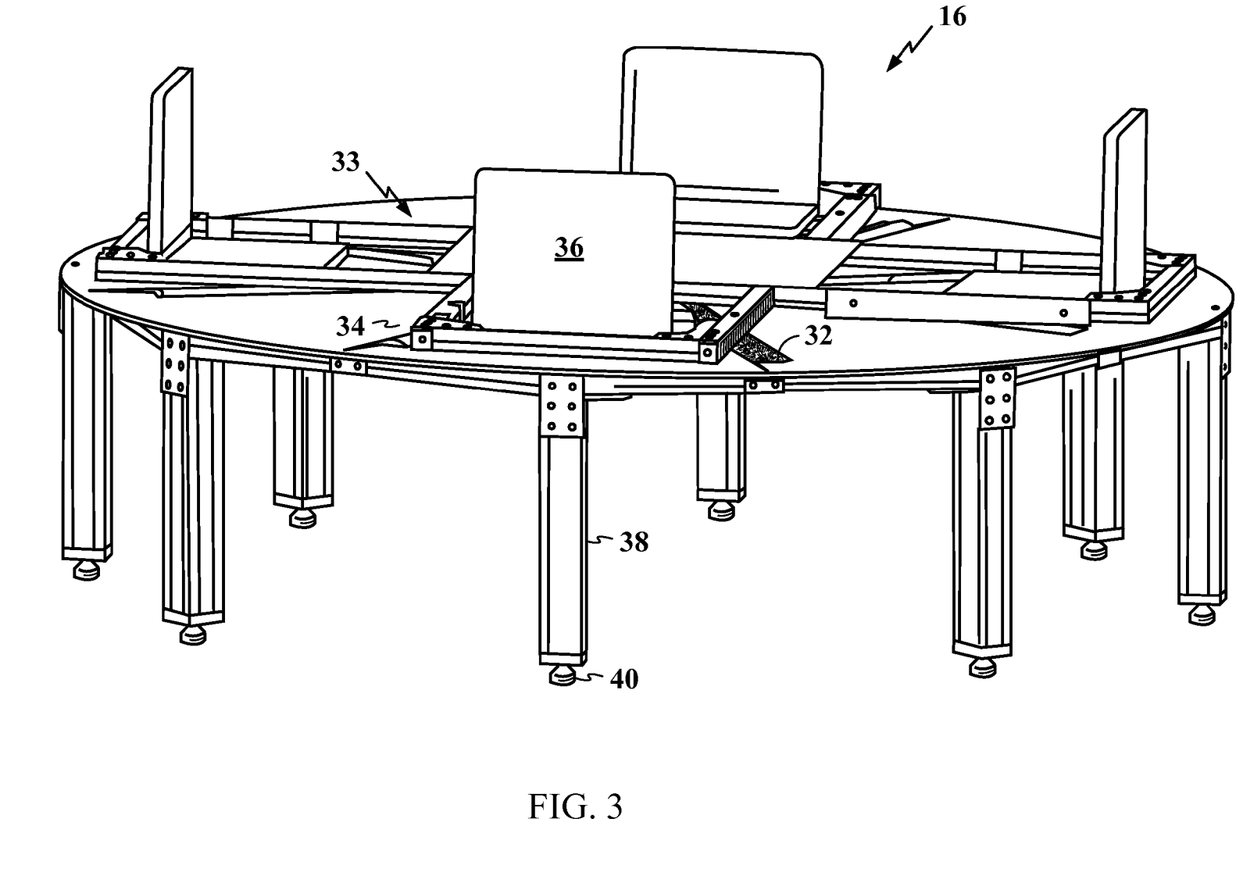
FIG. 3 shows selected aspects of a platform in the disclosed embodiment.

FIG. 3 shows selected aspects of platform 16 which, in the disclosed embodiment, takes the form of an 8-legged table including a set of rotating brushes 32 positioned within platform surface 33. Platform 16 includes rotating brushes 32 and electronic system brackets 34, each for holding an electronic system, such as laptop computer 36. Each laptop computer 36, in rotating in its respective electronic system bracket 34 about the center of table 32, passes brush slot 38. Brush slot 38 includes a plurality of thick rotating brushes 32 for cleaning the bottom of each laptop computer 36. Particulate contamination cleaned from the bottom of each laptop computer 36, then falls through brush slot 38 to below platform 16. Platform 16 further includes legs 40, which may be further supported by shock-absorbing feet 42.

Figure 4:
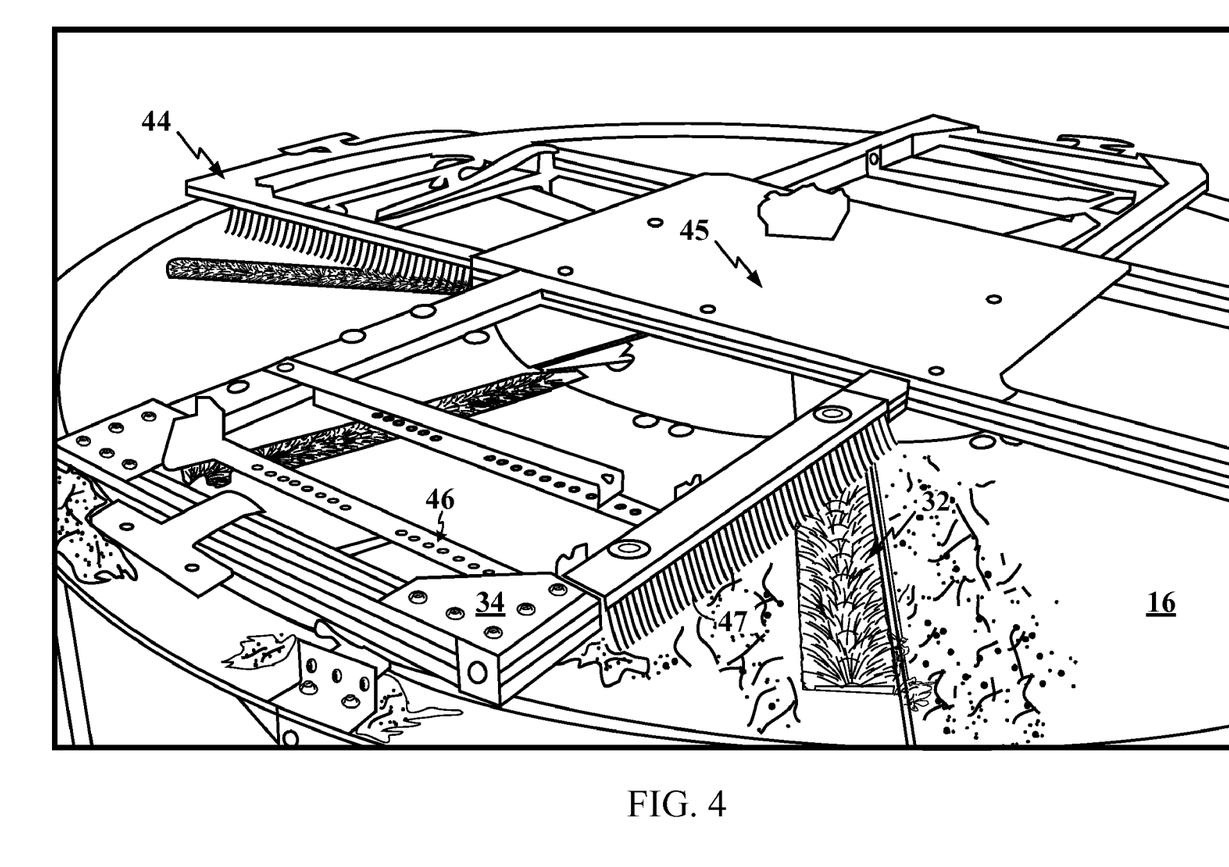
FIG. 4 depicts a turntable bracket of one embodiment of the disclosed subject matter for holding and moving laptop computers.
Figure 5:
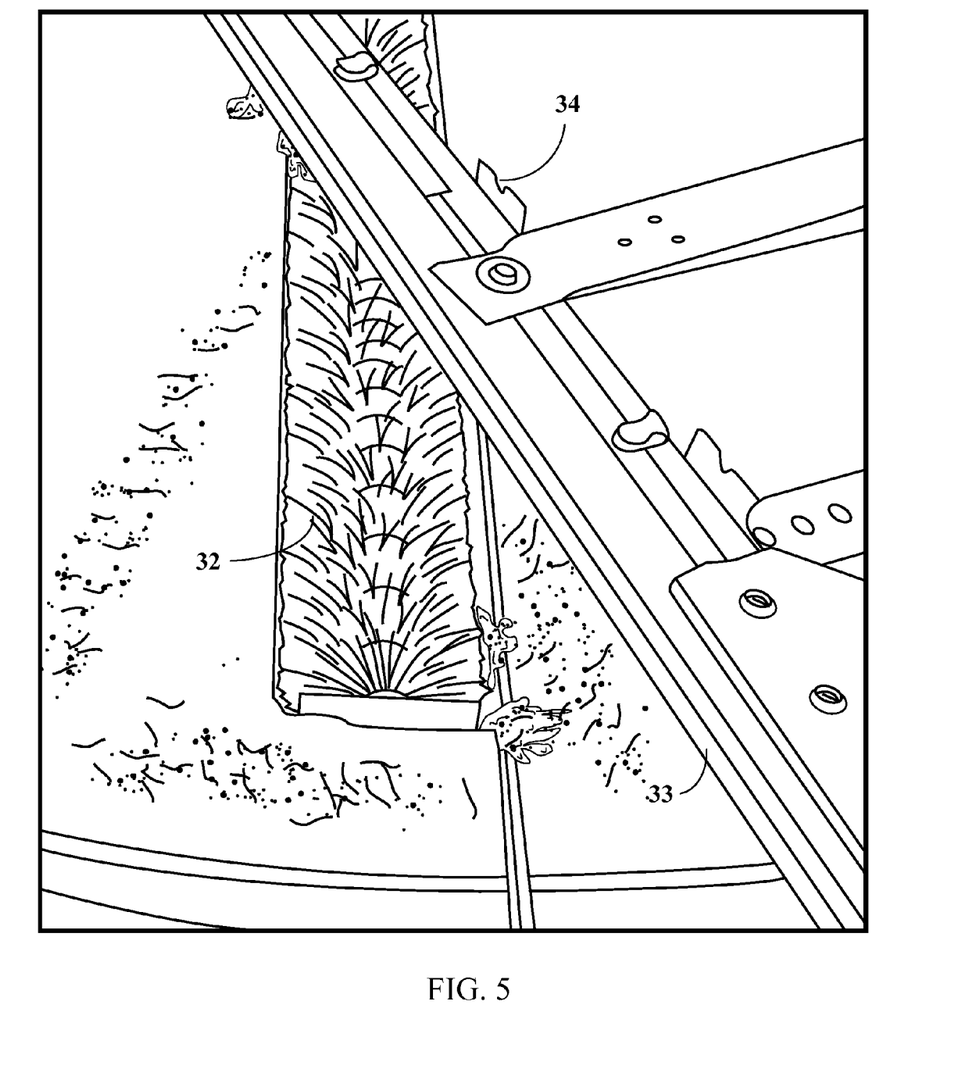
FIG. 5 displays a turntable bracket device for removing accumulated dust particles, as used in one embodiment of the disclosed subject matter.

FIG. 4 depicts one embodiment bracket turntable 44 including four electronic system brackets 34 according to the disclosed subject matter for holding. Bracket turntable 44 moves laptop computers 36 about axis 45 of platform 16. In the embodiment of FIG. 4, bracket turntable 44 includes four electronic system brackets 34, each of which may hold a laptop computer 36 using straps 46. Referring to FIGS. 4 and 5, as bracket turntable 44 rotates about axis 45, bristles on rotating brush 32 sweep the bottom portion of bracket 34 to remove accumulated dust particles. At the same time bristles from sweeper brushes 47 sweep the platform 16 surface clean, making way for new dust to settle.

Platform 16 provides, in one embodiment, a bolted together design that uses a DC motor for providing the rotating force for bracket turntable 44. The rotating element for bracket turntable 44 provides a controllable, variable rotation speed control and permits variable size electronic systems for testing. In one implementation, platform 16 may be finally assembled in environmental chamber 14 to assure a maximum size and efficient portability. Platform surface 33 preferably is antistatic and allows for a maximum size for placement within environmental chamber 14. In the present embodiment, platform 16 has sufficient strength to accommodate even large servers or computers for electronic systems environmental testing.

Bracket turntable 44 performs two main functions: (a) assuring settling (active airborne) dust test uniformity for up to four samples, in the present embodiment, by periodic rotating around the platform axis 45. Electronic systems under test are shifted 22.5 degrees on each move. In current testing methods, each unit will be positioned in each of eight locations six times in eight hours of testing.

Platform 16 also provides for passive contaminant or dust testing of electronic systems. Passive contaminants are those that have previously settled on surfaces, such as platform surface 33. However, passive contaminants also may arise from dust producing materials such as clothing or carpets where a laptop computer 36, for example, may rest. Bracket turntable 44 moves the electronic systems to pre-dusted locations on platform surface 33 for simulating placing the electronic systems on a contaminated surfaces in a real environment. Sweeper brushes 47 located behind and integral to electronic system brackets 34 clear the current location on platform surface 33 when the next rotation shift of bracket turntable 44 occurs. Sweeper brush 47 action also ensures that only one period of settled dust is present when the electronic system arrives at a new location on platform surface 33. In such process, rotating brush 32 clears any bottom inlet accumulations during the shift. This action of rotating brush 32 prevents a natural filter from forming on the air grillwork 80 of intake 78. This action also simulates the normal clearing action that occurs through handling and simulates direct contact of dust producing materials. Rotating brushes 32 also clear sweeper brushes 47 as they pass, thereby eliminating dust overburden throughout the test.

Because of rotating the electronic systems about the table center axis, a uniform distribution of airborne contaminants reaches each electronic system on the platform 16. In addition, by automatically mechanically cleaning bottom air inlets at short intervals, platform 16 provides prevents the blocking accumulation of dust or particulate that may prevent such particulate from entering and adversely affecting—for testing purposes—the introduction through the air inlets of such particles.

Figure 6:
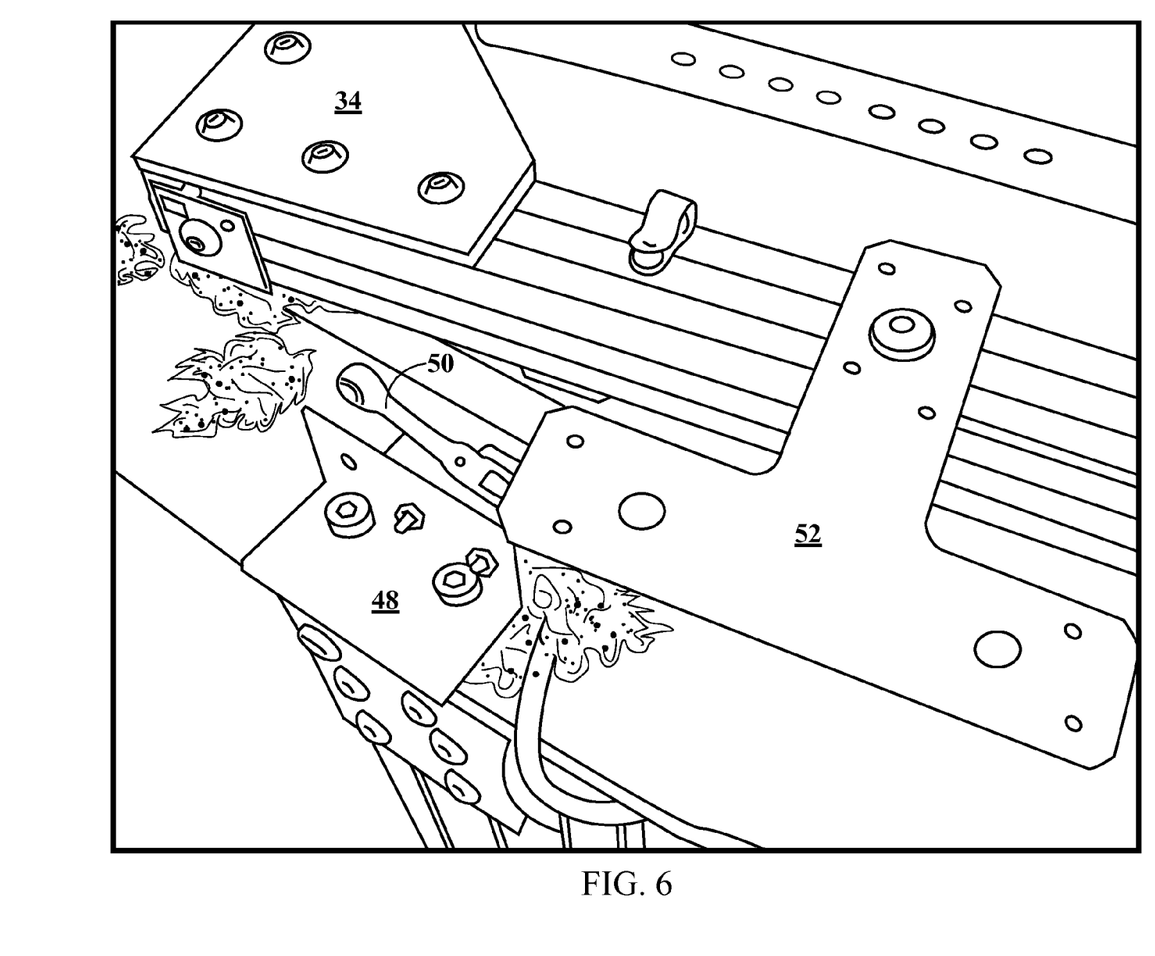
FIG. 6 shows a mechanism for controlling the motion of turntable bracket device.

FIG. 6 shows a further feature of the present embodiment, which includes a mechanism for controlling the motion of bracket turntable 44. In order to assure proper mechanical control of the rotation of bracket turntable 44, platform 16 includes a paddle switch 48. Paddle switch 48 includes actuator 50. Thus, as bracket turntable 44 rotates, Tee plate 52 at electronic system bracket 34 engages and depresses actuator 50. This closes a circuit associated with paddle switch 48, causing bracket turntable 44 to stop rotating. Then, upon actuation by the operator or an automated mechanism, further motion of bracket turntable 44 may resume.

Although many different embodiments of the disclosed subject matter arise, platform 16 may include includes a platform surface 33 supported by numerous leg assemblies of legs 38 and shock-absorbing feet 40 along with appropriate screws and joining hardware for their construction. The 80/20, Inc. of Columbia City, Ind. provides aluminum framing products and accessories suitable for such purposes. A platform surface 33 may be provided by Everest Manufacturing, while the rotating assembly of rotating brush 32 which may be formed of aluminum. For the rotating assemblies of bracket turntable 44 and rotating brush 32, Grainger Corporation may supply the appropriate gear motor assemblies. For rotating brush 32, Carolina Brush may provide, for example, an 18" long, 3" diameter nylon brush, as well as the straight sweeper brush.

For controlling the motion of frame, paddle switch 48 also may be provided by Grainger Manufacturing. Furthermore, each electronic system bracket may include a plurality of nylon glide surfaces to promote a lower friction as the bracket rotates on the dust platform surface.

Figure 7:
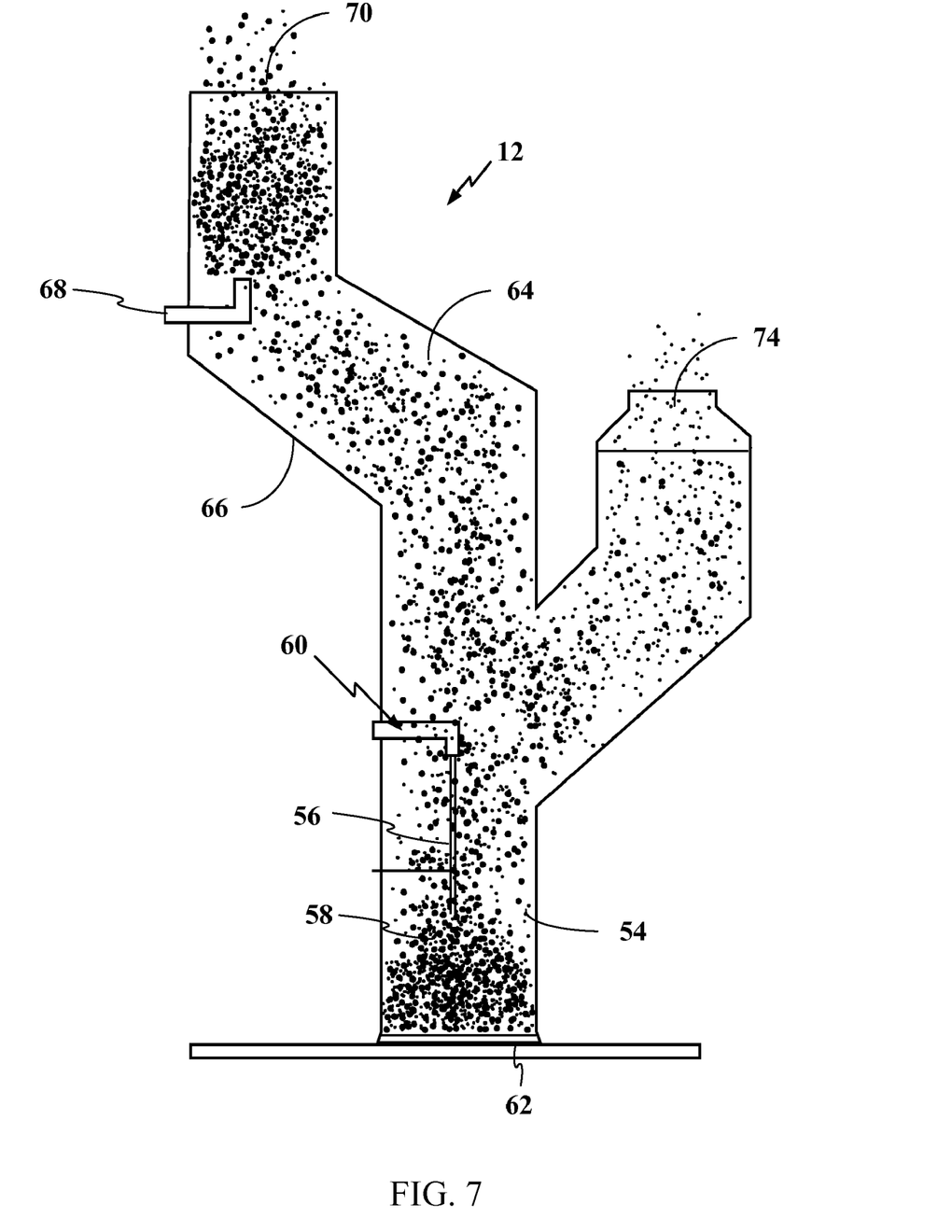
FIGS. 7 and 8 show views of a contaminant delivery system particulate contamination according to the present teachings.
Figure 8:
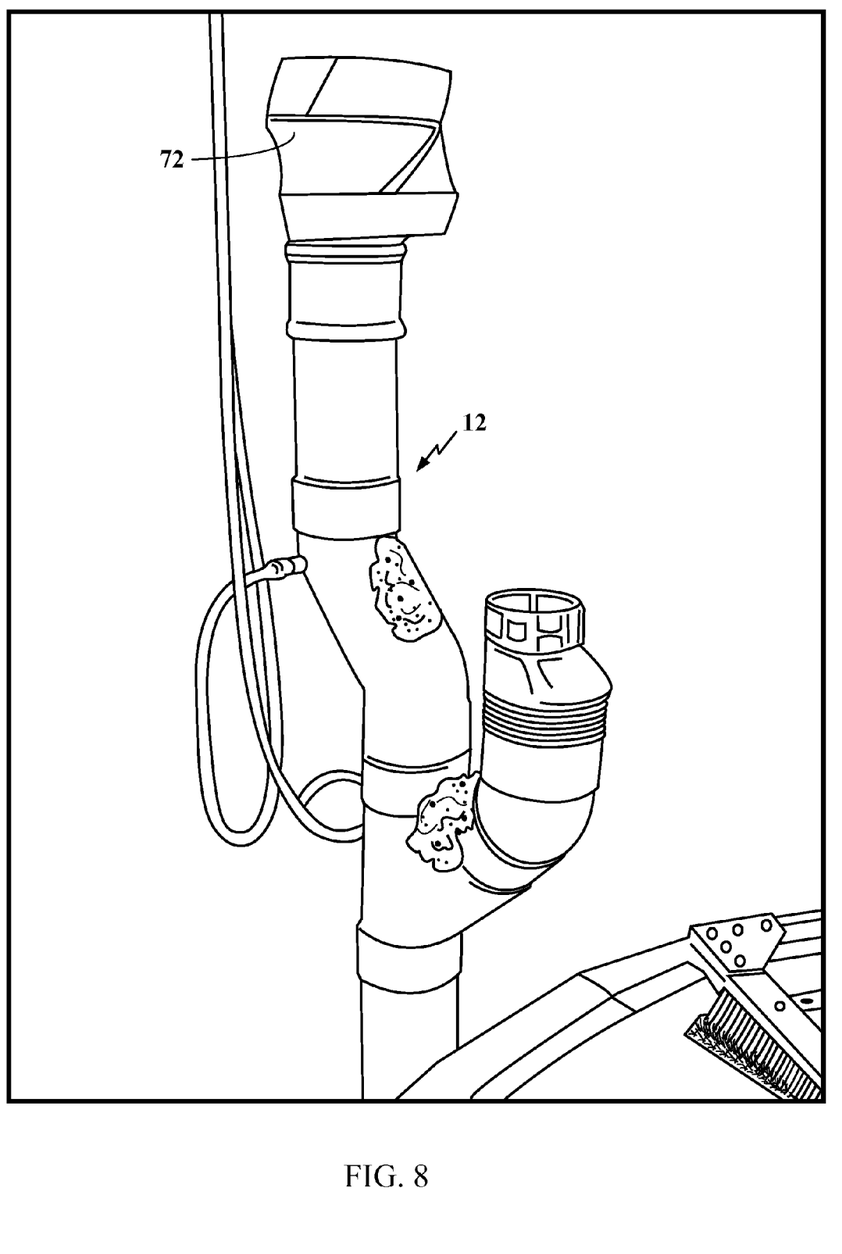

FIG. 7 provides a schematic cross-sectional view and FIG. 8 shows a conceptual operational diagram of contaminant delivery system 12 for delivering airborne contaminants contamination, such as dust, into environmental chamber 14. Contaminant delivery system 12 includes clasting chamber 54, which further includes randomizer 56. Randomizer 56, in the disclosed embodiment, takes the form of an elastic hose 58 through which a stream of compressed air flows, which air comes from pipe 60. Because of the length and flexibility of elastic hose 58, as compressed air flows a whipping action occurs. The whipping action causes elastic hose 58 to stir and mix particulate 62 within clasting chamber 54 to form airborne contaminants 64. Airborne particulate 64 flows upward in pipe 66 of contaminant delivery system 12 to and past high-pressure air flow pipe 68 and outward via exhaust opening 70. The pressures from air flow pipe are nominal 80 to 90 psi via a standard quarter inch hose and controlled using a $3/8$ solenoid valve.

Figure 9:
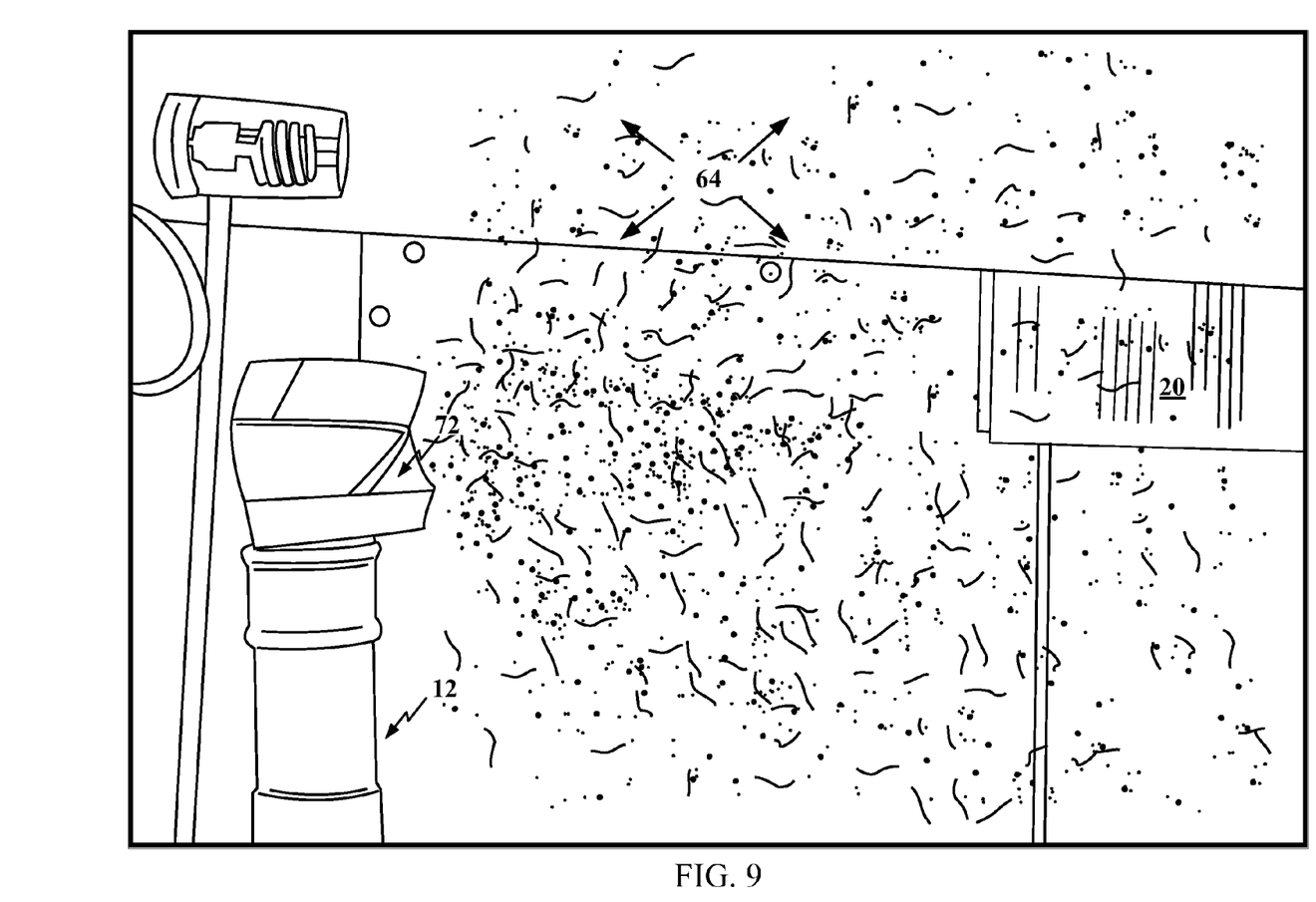
FIG. 9 shows use a directing piece with the disclosed subject matter.

As FIG. 9 shows, contaminant delivery system 12 may further include director 72 for providing a more directed flow of particulate contamination into environmental chamber 12. FIG. 7, therefore, shows more particularly the spray or distribution of particulate contamination. The result of operation of contaminant delivery system 12 is that particulate 62 becomes airborne particulate 64 that may deposit or settle in significant amounts on platform 16.

Thus, referring collectively to FIGS. 7 through 9, in operation the operation of contaminant delivery system 12, particulate or dust enters inlet 74 (FIG. 7) and falls by gravity to clasting chamber 54. Then, by whipping about, randomizer 56 blows, stirs and causes the particulate or dust to flow upward in pipe 66. Once in the proximity of high-pressure airflow pipe 68, the airborne particulate 64 flows with energy out of exhaust 70 and further flows via director 72 toward platform 16. Accordingly, contaminant delivery system 12 uses a venturi device based on the Bernoulli Principle of pumping air through the generator at high volumes. Randomizer 56 loosens the matted fibers in clasting chamber 54 and provides enough airflow to propel the lightweight individual fiber dusts, in one embodiment of particulate 62 upward to mix with the higher volume airflow. The heavier clustered-clumps remain in the clasting chamber for further division. Independently regulated pressures for the randomized stir input 60 and the jet pump dispensing flow pipe 68, combined with adjustable inject and settle timings, allow for variation in dust injection densities and calibration.

Figure 10:
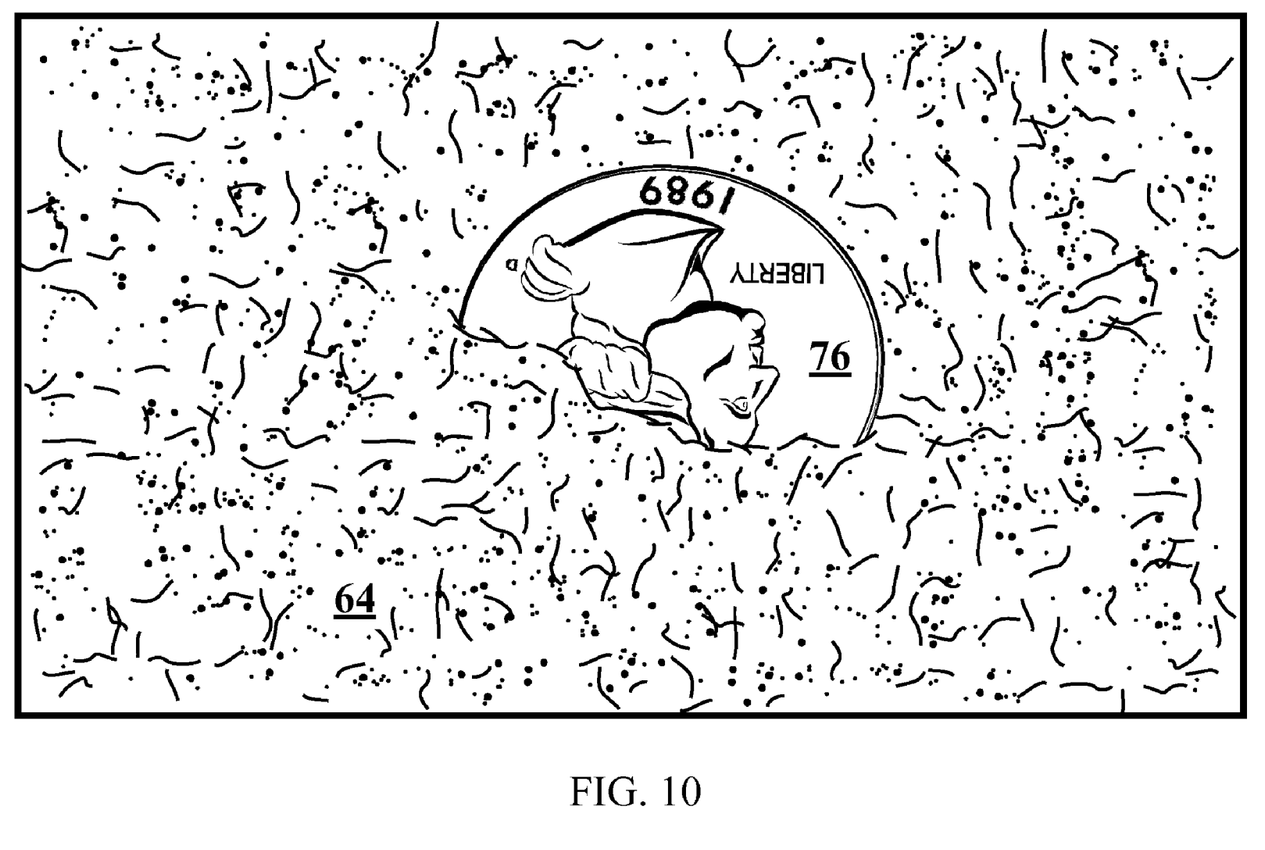
FIGS. 10 and 11 show certain aspects of the effectiveness of the disclosed subject matter.
Figure 11:
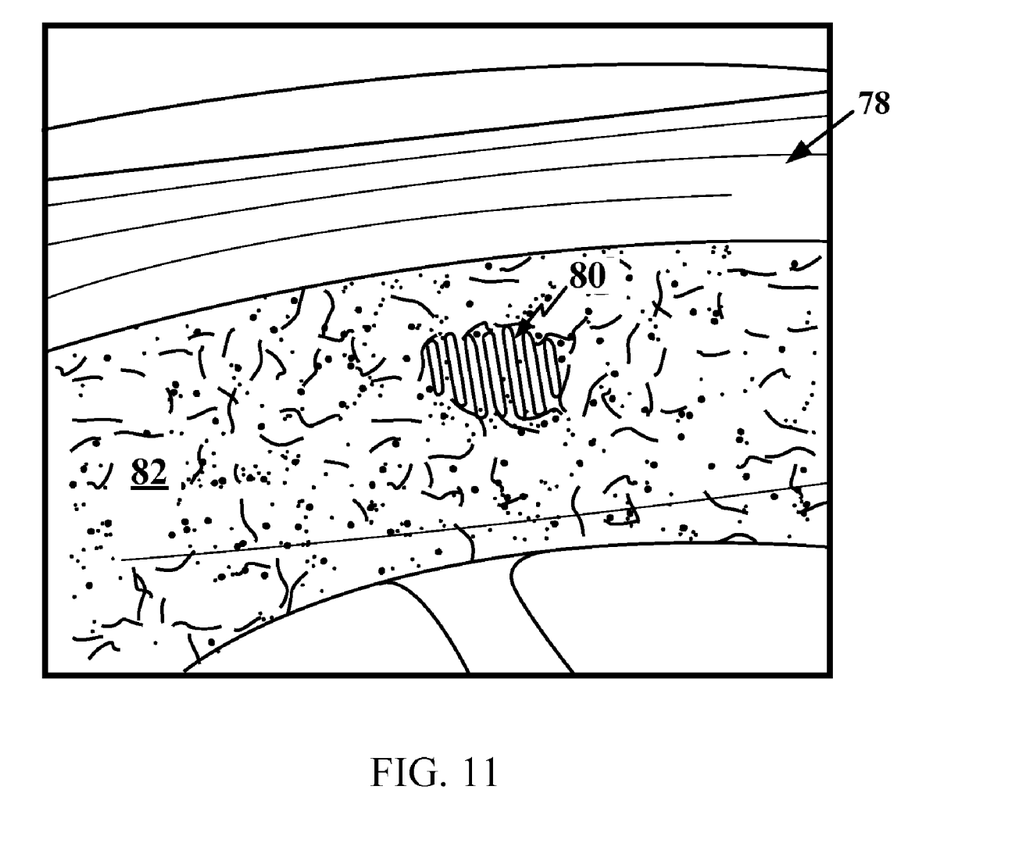

FIGS. 10 and 11 show the effectiveness of contaminant delivery system 12 in forming significant levels of settled particulate 64. That is, referring to FIG. 10, clearly the level of dust, which accumulates over a sixteen-hour period—almost one-half the height of U.S. quarter 76—is substantial enough to promote testing of the adverse effects of such contamination. In fact, referring further to FIG. 11, laptop computer air intake 78 shows such accumulation at grillwork 80 as would cause seriously adverse effects for the operation of a laptop computer 36.

The present disclosure may make use of a dust compound, for example, the includes concentrations of fine dust and fibers that, while airborne, induce a maximum amount of failure, as well as the ability to provide for consistent concentrations of dust throughout the environmental chamber.

In further understanding environmental contaminant testing system 10, will be appreciated that passive dust or "settled dust" testing is now practical. Using environmental contaminant testing system 10, electronic systems, such as laptop computers 36, may be placed on a pre-dusted platform surface 33. The environmental contaminant testing system 10 provides the ability to clean air intakes 78 and move the electronic systems to a location of platform surface 33 at regular intervals, e.g., every 10 minutes. Then, a process may include remove the electronic systems and clean the portion of platform surface 33 on which the particulate or dust had settled. Such a process may continue through numerous iterations.

In such testing, concerns such as high concentrations of long fibers, low accumulations of fine dust and short fiber accumulations, and other labor intensive and long test duration scenarios may be addressed. The environmental contaminant testing system 10 may accommodate the testing with an entire host of particulate or dust mixtures in current chamber. One such mixture affords an optimal level of testing automation and uniformity issue.

For promoting measurable and repeatable analyses, the disclosed subject matter makes use of a standard dust mixture. For example, one dust mixture is composed of 25% 2 mm nylon, 25% mm polypropylene, 10% 12 mm nylon, 30% cotton linters, and 10% ISO-fine test dust. Another dust mixture may include 22.5% 2 mm nylon, 22.5% 3 mm polypropylene, 5% 12 mm nylon, 20% linters, and 30% ISO-fine test dust.

The disclosed subject matter provides an optimal combination of active and passive dust testing methods in a single system. In addition, the disclosed system improves uniformity of dust as the electronic systems moves from location to location. Using an optimal dust mixture with humidity and temperature control, the disclosed system makes possible reliable testing for a wide variety of potential particulate contamination evaluation scenarios.

For example, one evaluation may be to determine the effects of passive or "settled" dust. In such a test, an operator may place operational electronic systems on pre-dusted surface of table. The process may next call for cleaning inlet vents and moving the electronic systems to new surface location every 10 minutes. After six such moves, the operator may remove units clean surface re-dust surface. Such steps may be repeated for a predetermined period, e.g., 16 hours, or until failure occurs.

One desirable current test method requires an hourly overall external "dust off" cleaning of the electronic systems at which time the contaminant delivery system 12. Digital input to chamber control cabinet 22 restarts the system hourly. At the completion of an hour-long cycle, a controller in chamber control cabinet 22 waits for an operator signal supplied by a switch located on the front panel of chamber control cabinet 22. Once the operator completes the cleaning and loading task he depresses the switch to activate digital input which starts the next cycle.

The processing features and functions described herein can be implemented in various manners. The foregoing description of the preferred embodiments, therefore, is provided to enable any person skilled in the art to make or use the claimed subject matter. Various modifications to these embodiments will be readily apparent to those skilled in the art, and the generic principles defined herein may be applied to other embodiments without the use of the innovative faculty. Thus, the claimed subject matter is not intended to be limited to the embodiments shown herein but is to be accorded the widest scope consistent with the principles and novel features disclosed herein.

What is claimed is:

1. A platform for holding electronic devices during environmental testing, comprising:
   a surface for providing vertical support;
   a plurality of bracket mechanisms associated with said surface, each of said bracket mechanisms for holding in position an electronic device;
   a bracket positioning mechanism for associating with said plurality of bracket mechanisms for controllably positioning said bracket mechanisms;
   a control mechanism associated with said bracket positioning mechanism for controlling the positioning of said bracket mechanisms; and
   at least one brush mechanism positioned in associated with said bracket mechanisms for brushing said bracket mechanisms and an electronic device held in position by said bracket mechanism.

2. The platform of claim 1, wherein said at least one brush mechanism comprises at least one rotating brush mechanism positioned for rotating and brushing said bracket mechanism and an associated electronic device, thereby removing particulate contamination from said bracket mechanism and said electronic device.

3. The platform of claim 1, wherein said bracket positioning mechanism comprises a bracket turntable for rotating said plurality of bracket mechanisms about a platform axis.

4. The platform of claim 1, further comprising a bracket turntable for performing active particulate contamination testing and comprising a sweeper brush for cleaning said surface in the rotation of said bracket turntable, thereby providing a cleaned surface for particulate contamination deposition.

5. The platform of claim 1, further comprising a bracket turntable for performing passive particulate contamination testing, said bracket turntable for positioning said bracket mechanism and an electronic device proximate to particulate contamination present on said surface.

6. The testing platform of claim 1, wherein said surface, said bracket mechanism, said bracket positioning mechanism may be finally assembled in an environmental chamber.

7. The testing platform of claim 1, wherein said surface further comprises an anti-static surface.

8. The testing platform of claim 1, each of said bracket mechanisms for holding in position variable size electronic devices.

9. The testing platform of claim 1, wherein said surface, said bracket mechanism, and said bracket positioning mechanism are formed of sufficiently strong materials for particulate contamination testing of computer server units.

10. The testing platform of claim 1, wherein said control mechanism further comprises a variable rate control mechanism for variably controlling the rate of movement of said bracket mechanism.

11. The testing platform of claim 4, said at least one brush mechanism for cleaning said sweeper brush.

12. An airborne contaminants testing system for testing the operation of electronic systems in response to an accumulation of airborne contaminants within the electronic systems, comprising:

an environmental chamber for containing a plurality of electronic devices, the electronic devices comprising air intake mechanisms, the air intake mechanisms susceptible to receiving the airborne contaminants and excessively heat in response to accumulated settled amounts of the airborne contaminants within the air intake mechanisms; and a platform for holding the electronic devices during environmental testing, said platform comprising:

a surface for providing vertical support;

a plurality of bracket mechanisms associated with said surface, each of said bracket mechanisms for holding in position an electronic device;

a bracket positioning mechanism for associating with said plurality of bracket mechanisms for controllably positioning said bracket mechanisms;

a control mechanism associated with said bracket positioning mechanism for controlling the positioning of said bracket mechanisms; and at least one brush mechanism positioned in associated with said bracket mechanisms for brushing said bracket mechanisms and an electronic device held in position by said bracket mechanism.

13. The system of claim 12, wherein said at least one brush mechanism comprises at least one rotating brush mechanism positioned for rotating and brushing said bracket mechanism and an associated electronic device, thereby removing particulate contamination from said bracket mechanism and said electronic device.

14. The system of claim 12, wherein said bracket positioning mechanism comprises a bracket turntable for rotating said plurality of bracket mechanisms about a platform axis.

15. The system of claim 12, further comprising a bracket turntable for performing active particulate contamination testing and comprising a sweeper brush for cleaning said surface in the rotation of said bracket turntable, thereby providing a cleaned surface for particulate contamination deposition.

16. The system of claim 12, wherein said surface, said bracket mechanism, said bracket positioning mechanism may be finally assembled in said environmental chamber.

17. The system of claim 15, said at least one brush mechanism for cleaning said sweeper brush.

18. A method for holding and positioning electronic devices during environmental testing, comprising the steps of:

providing vertical support for said electronic devices using a surface;

associating with said surface a plurality of bracket mechanisms and holding in position an electronic device with at least one of said bracket mechanisms;

associating with said plurality of bracket mechanisms a bracket positioning mechanism and controllably positioning said bracket mechanisms using said bracket positioning mechanism;

associating a control mechanism with said bracket positioning mechanism and controlling the positioning of said bracket mechanisms using said control mechanism; and positioning at least one brush mechanism in association with said bracket mechanisms for brushing said bracket mechanisms and an electronic device.

19. The method of claim 18, further comprising the step rotating at least one brush mechanism and brushing said bracket mechanism and an associated electronic device, thereby removing particulate contamination from said bracket mechanism and said electronic device.

20. The method of claim 18, further comprising the step of rotating said plurality of bracket mechanisms about a platform axis.

* * * * *